(12) United States Patent
Barker

(10) Patent No.: US 9,510,857 B2
(45) Date of Patent: Dec. 6, 2016

(54) SYSTEM AND METHOD FOR MAKING AND USING A LEAD INTRODUCER FOR AN IMPLANTABLE ELECTRICAL STIMULATION SYSTEM

(75) Inventor: John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1133 days.

(21) Appl. No.: 13/038,929

(22) Filed: Mar. 2, 2011

(65) Prior Publication Data

US 2011/0224680 A1 Sep. 15, 2011

Related U.S. Application Data

(60) Provisional application No. 61/312,621, filed on Mar. 10, 2010.

(51) Int. Cl.
| | |
|---|---|
| A61B 19/00 | (2006.01) |
| A61B 17/34 | (2006.01) |
| A61N 1/05 | (2006.01) |
| A61N 1/36 | (2006.01) |
| A61M 25/01 | (2006.01) |
| A61M 25/06 | (2006.01) |

(52) U.S. Cl.
CPC ......... *A61B 17/3468* (2013.01); *A61N 1/0551* (2013.01); *A61N 1/36071* (2013.01); *A61M 25/0102* (2013.01); *A61M 25/0668* (2013.01)

(58) Field of Classification Search
CPC ............... A61B 17/3468; A61M 25/0102; A61M 25/0668; A61N 1/0551; A61N 1/36071

USPC ......... 606/129; 604/164.01, 164.05; 607/117
See application file for complete search history.

(56) References Cited

U.S. PATENT DOCUMENTS

| | | | |
|---|---|---|---|
| RE31,855 | E | 3/1985 | Osborne |
| 4,512,351 | A * | 4/1985 | Pohndorf ...................... 607/117 |
| 5,125,904 | A | 6/1992 | Lee |
| 5,320,602 | A | 6/1994 | Karpiel |
| 5,409,469 | A | 4/1995 | Schaerf |
| 5,441,504 | A | 8/1995 | Pohndorf et al. |
| 5,443,492 | A | 8/1995 | Stokes |
| 5,713,867 | A | 2/1998 | Morris |
| 5,741,233 | A | 4/1998 | Riddle et al. |
| 5,752,937 | A | 5/1998 | Otten et al. |
| 5,755,693 | A | 5/1998 | Walker et al. |
| 6,080,141 | A | 6/2000 | Castro et al. |
| 6,181,969 | B1 | 1/2001 | Gord |
| 6,251,119 | B1 | 6/2001 | Addis |
| 6,358,460 | B1 | 3/2002 | Hunt, Jr. et al. |

(Continued)

*Primary Examiner* — Diane Yabut
*Assistant Examiner* — Martin T Ton
(74) *Attorney, Agent, or Firm* — Lowe Graham Jones PLLC; Bruce E. Black

(57) ABSTRACT

A lead introducer includes a multi-piece insertion needle insertable into a splitable member. The multi-piece insertion needle includes an outer insertion needle that defines an open channel that extends along substantially entirely a length of the outer insertion needle and an inner insertion needle configured and arranged for insertion into the open channel of the outer insertion needle. The splitable member includes at least two pull-apart tabs and at least one weakened region extending along at least a portion of a length of the splitable member from between the at least two pull-apart tabs. The at least one weakened region is configured and arranged for separating when the at least two pull-apart tabs are pulled apart.

20 Claims, 12 Drawing Sheets

(56) References Cited

U.S. PATENT DOCUMENTS

| | | |
|---|---|---|
| 6,454,744 B1 | 9/2002 | Spohn et al. |
| 6,494,860 B2 | 12/2002 | Rocamora et al. |
| 6,516,227 B1 | 2/2003 | Meadows et al. |
| 6,582,390 B1 | 6/2003 | Sanderson |
| 6,609,029 B1 | 8/2003 | Mann et al. |
| 6,609,032 B1 | 8/2003 | Woods et al. |
| 6,641,564 B1 * | 11/2003 | Kraus .................. 604/164.1 |
| 6,645,178 B1 | 11/2003 | Junker et al. |
| 6,712,791 B2 | 3/2004 | Lui et al. |
| 6,741,892 B1 | 5/2004 | Meadows et al. |
| 6,749,600 B1 | 6/2004 | Levy |
| 6,758,854 B1 | 7/2004 | Butler et al. |
| 6,869,416 B2 * | 3/2005 | Windheuser et al. ... 604/164.05 |
| 6,939,327 B2 | 9/2005 | Hall et al. |
| 7,001,396 B2 | 2/2006 | Glazier et al. |
| 7,014,626 B2 | 3/2006 | Sanderson |
| 7,101,353 B2 | 9/2006 | Lui et al. |
| 7,192,433 B2 | 3/2007 | Osypka et al. |
| 7,244,150 B1 | 7/2007 | Brase et al. |
| 7,524,305 B2 | 4/2009 | Moyer |
| 7,672,734 B2 | 3/2010 | Anderson et al. |
| 7,744,571 B2 | 6/2010 | Fisher et al. |
| 7,761,165 B1 | 7/2010 | He et al. |
| 7,792,590 B1 | 9/2010 | Pianca |
| 7,887,733 B2 | 2/2011 | Moyer |
| 7,909,798 B2 | 3/2011 | Osypka |
| 7,938,806 B2 | 5/2011 | Fisher et al. |
| 7,941,227 B2 | 5/2011 | Barker |
| 7,985,232 B2 | 7/2011 | Potter et al. |
| 7,993,305 B2 | 8/2011 | Ye et al. |
| 8,043,263 B2 | 10/2011 | Helgeson et al. |
| 8,105,287 B2 | 1/2012 | Fisher et al. |
| 8,105,315 B2 | 1/2012 | Johnson et al. |
| 8,147,456 B2 | 4/2012 | Fisher et al. |
| 8,273,059 B2 | 9/2012 | Nardeo et al. |
| 2003/0114905 A1 | 6/2003 | Kuzma |
| 2005/0165465 A1 | 7/2005 | Pianca et al. |
| 2007/0150036 A1 | 6/2007 | Anderson |
| 2007/0219595 A1 | 9/2007 | He |
| 2007/0239243 A1 | 10/2007 | Moffitt et al. |
| 2008/0071320 A1 | 3/2008 | Brase |
| 2008/0103570 A1 * | 5/2008 | Gerber .................. 607/115 |
| 2011/0218549 A1 | 9/2011 | Barker |
| 2011/0224681 A1 | 9/2011 | McDonald |
| 2011/0230893 A1 | 9/2011 | Barker |

\* cited by examiner

SYSTEM AND METHOD FOR MAKING AND USING A LEAD INTRODUCER FOR AN IMPLANTABLE ELECTRICAL STIMULATION SYSTEM

CROSS-REFERENCE TO RELATED APPLICATIONS

This application claims the benefit under 35 U.S.C. §119 (e) of U.S. Provisional Patent Application Ser. No. 61/312,621 filed on Mar. 10, 2010, which is incorporated herein by reference.

FIELD

The present invention is directed to the area of implantable electrical stimulation systems and methods of making and using the systems. The present invention is also directed to a lead introducer for facilitating insertion of implantable electrical stimulation leads having non-isodiametric lead bodies into patients, as well as methods of making and using the lead introducers and electrical stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead introducer includes a multi-piece insertion needle and a splitable member. The multi-piece insertion needle includes an outer insertion needle and an inner insertion needle. The outer insertion needle includes a proximal hub and defines an open channel that extends along substantially entirely a length of the outer insertion needle. The inner insertion needle includes a proximal hub and defines a lumen that extends from the proximal hub along substantially entirely a length of the inner insertion needle. The inner insertion needle is configured and arranged for insertion into the open channel of the outer insertion needle. The splitable member includes a proximal hub and defines a lumen configured and arranged for receiving at least a portion of the multi-piece insertion needle. The splitable member includes at least two pull-apart tabs disposed on the proximal hub of the splitable member and at least one weakened region extending along at least a portion of a length of the splitable member from between the at least two pull-apart tabs. The at least one weakened region is configured and arranged for separating when the at least two pull-apart tabs are pulled apart from one another in directions approximately orthogonal to the splitable member.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to a lead introducer for facilitating insertion of implantable electrical stimulation leads having non-isodiametric lead bodies into patients, as well as methods of making and using the lead introducers and electrical stimulation leads.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. Patent Applications Publication Nos. 2003/0114905, 2005/0165465, 2007/0150036; 2007/0161294; 2007/0219595; 2007/0239243; 2007/0150007; and 2008/0071320, and U.S. patent application Ser. No. 11/238,240, all of which are incorporated by reference.

Figure 1:
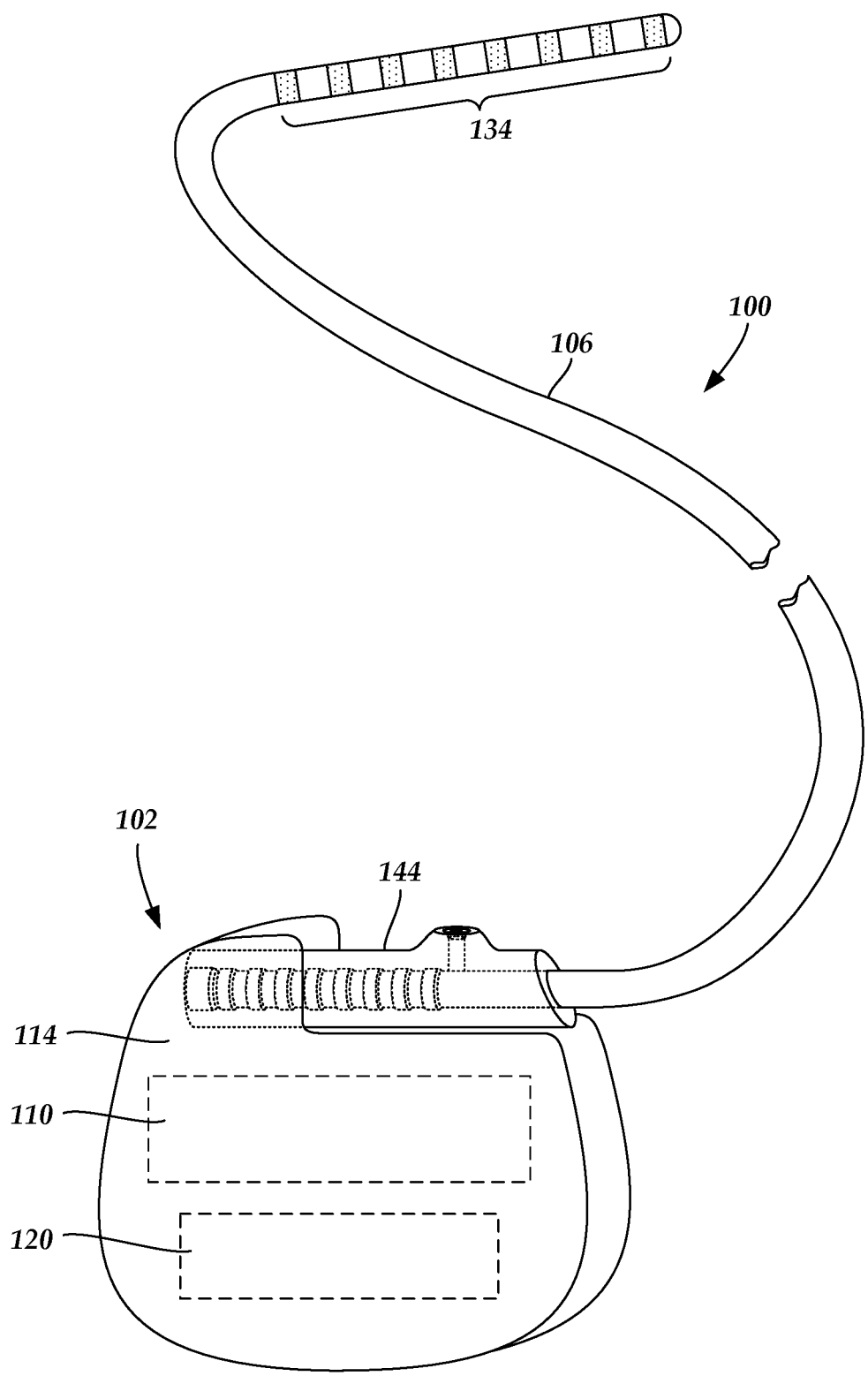
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead 106 coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIG. 2A and 236 of FIG. 2B) on each of the one or more leads 106. In at least some embodiments, a lead is isodiametric along a longitudinal length of the lead 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 2B) is only connected to one electrode 134. The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet rod to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
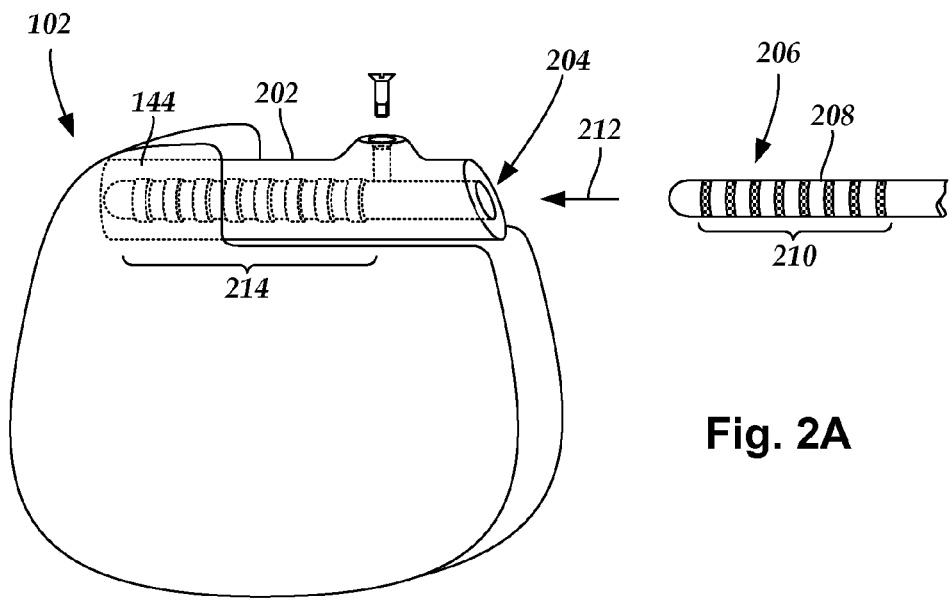
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208.

Examples of connectors in control modules are found in, for example, U.S. Pat. No. 7,244,150 and U.S. patent application Ser. No. 11/532,844, which are incorporated by reference.

Figure 2B:
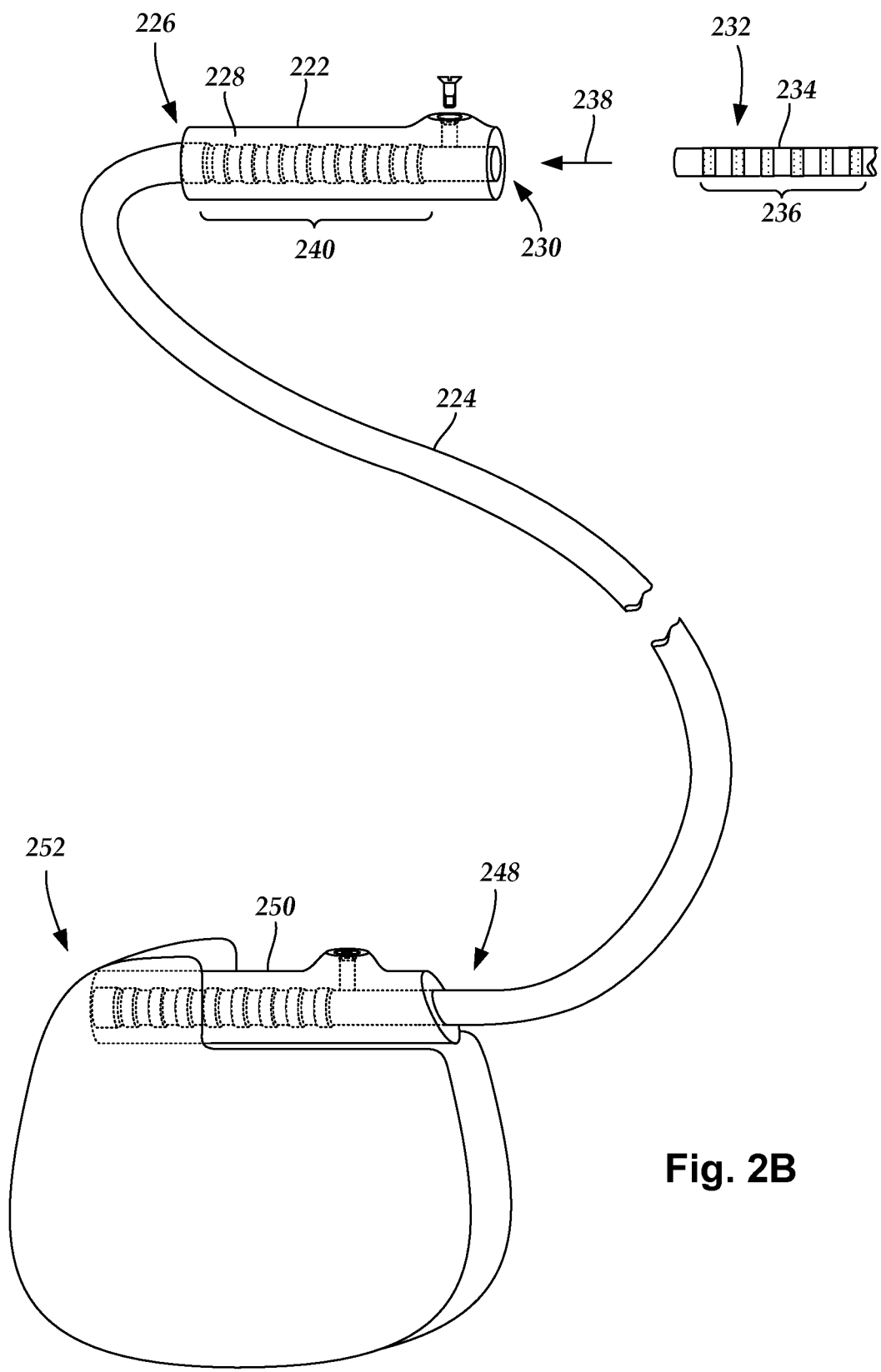
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Some conventional percutaneous implantation techniques involve inserting a lead introducer, such as an epidural needle, into a patient. Once the lead introducer is inserted into the patient, a lead is inserted into the lead introducer and the lead introducer is positioned at a target stimulation location. Once the lead introducer is positioned at the target stimulation location, the lead introducer is removed from the patient, leaving the lead in place. Typically, the lead introducer is removed from the patient by sliding the lead introducer off the proximal end of the lead.

Unfortunately, when a lead has a body that is not isodiametric, it may be difficult to slide the lead introducer off the proximal end of the lead. For example, when a proximal end of a lead body has a diameter that is larger than a distal end of the lead body, or when an oversized junction or adapter is disposed along the length of the lead body, the varying diameters along the length of the lead body may hinder, or even prevent, the lead introducer from sliding off the proximal end of the lead.

A lateral-release lead introducer ("lead introducer") uses a multi-piece insertion needle that enables a lead to be laterally separated from the multi-piece insertion needle. In at least some embodiments, the lead may be laterally separated from the multi-piece insertion needle without sliding the multi-piece insertion needle off the proximal end of the lead. In at least some embodiments, the lead laterally separates from the multi-piece insertion needle by passing the lead through an open channel defined along a length of the multi-piece insertion needle. In at least some embodiments, during implantation of the lead the multi-piece insertion needle is disposed in a splitable member that separates from the lead by splitting apart along a length of the splitable member.

Figure 3:
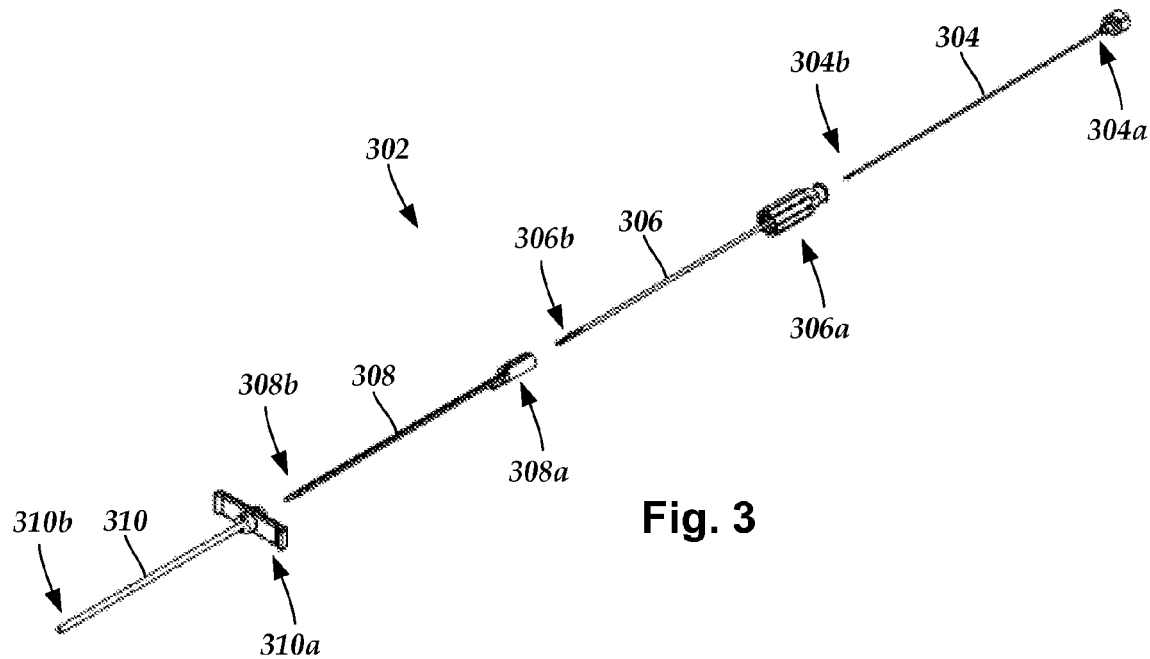
FIG. 3 is a schematic perspective exploded view of one embodiment of a lead introducer configured and arranged to facilitate implantation of an electrical stimulation system into a patient, according to the invention.

FIG. 3 is a schematic perspective exploded view of one embodiment of a lead introducer 302 configured and arranged to facilitate implantation of an electrical stimulation system into a patient. The lead introducer 302 includes an obturator 304, an inner insertion needle 306, an outer insertion needle 308, and a splitable member 310. The obturator 304 has a proximal hub 304a and a distal end 304b. The inner insertion needle 306 has a proximal hub 306a and a distal end 306b, and defines a lumen (not shown) extending from the proximal hub 306a. The outer insertion needle 308 has a proximal hub 308a and a distal end 308b, and defines an open channel (704 in FIG. 7) extending along a length of the outer insertion needle 308. The splitable member 310 has a proximal hub 310a and a distal end 310b, and defines a lumen (not shown) extending from the proximal hub 310a.

In at least some embodiments, the distal end 304b of the obturator 304 is configured and arranged for insertion into the lumen of the inner insertion needle 306. In at least some embodiment, the distal end 306b of the inner insertion needle 306 is configured and arranged for insertion into the open channel (704 in FIG. 7) of the outer insertion needle 308. In at least some embodiments, the distal end 308b of the outer insertion needle 308 is configured and arranged for insertion into the lumen of the splitable member 310.

Figure 4:
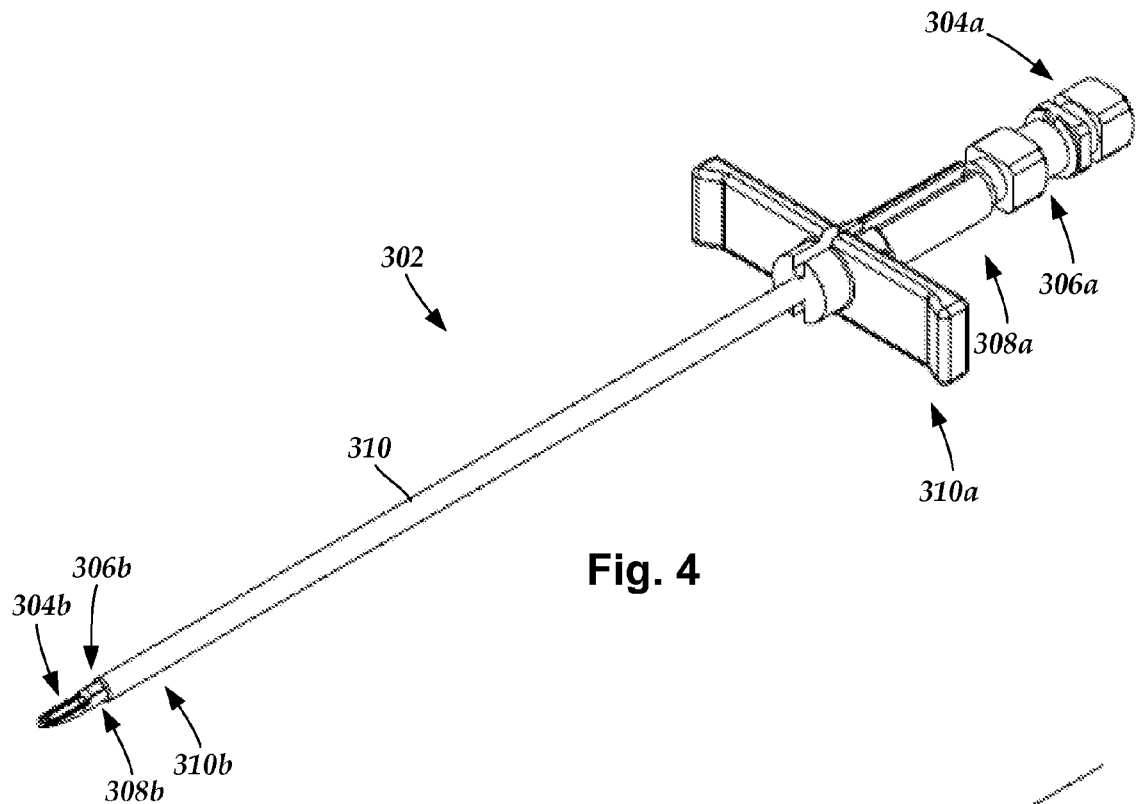
FIG. 4 is a schematic perspective view of one embodiment of the lead introducer of FIG. 3, according to the invention.

In at least some embodiments, the obturator 304, the inner insertion needle 306, the outer insertion needle 308, and the splitable member 310 are coupleable to one another such that the obturator 304, the inner insertion needle 306, the outer insertion needle 308, and the splitable member 310 form a nested arrangement. FIG. 4 is a schematic perspective view of one embodiment of the obturator 304 disposed in the inner insertion needle 306 which, in turn, is disposed in the outer insertion needle 308 which, in turn is disposed in the splitable member 310.

In at least some embodiments, the obturator 304, the inner insertion needle 306, the outer insertion needle 308, and the splitable member 310 are coupleable to one another such that the proximal hubs 304a, 306a, 308a, and 310a of the obturator 304, the inner insertion needle 306, the outer insertion needle 308, and the splitable member 310, respectively, align axially to one another. In at least some embodiments, the obturator 304, the inner insertion needle 306, the outer insertion needle 308, and the splitable member 310 are coupleable to one another such that the distal ends 304b, 306b, and 308b of the obturator 304, the inner insertion needle 306, and the outer insertion needle 308, respectively, extend distally beyond the distal end 310b of the splitable member 310.

In at least some embodiments, the outer insertion needle 308 is formed from a rigid material suitable for implantation, such as stainless steel. In at least some embodiments, the inner insertion needle 306 is formed from the same material as the outer insertion needle 308. In at least some embodiments, the inner insertion needle 306 is formed from a material that is more flexible than the outer insertion needle 308. In at least some embodiments, the outer insertion needle 308 is formed from a material that is more rigid than the splitable member 310. In at least some embodiments, the outer insertion needle 308 is formed from a material that is rigid enough to enable the outer insertion needle 308 to be used to guide (e.g., enable lateral steering) the splitable member 310 within a patient when the outer insertion needle 308 is disposed in the splitable member 310.

In at least some embodiments, the lateral circumference of the outer insertion needle 308 is no greater than sixteen-gauge. In at least some embodiments, the lateral circumference of the outer insertion needle 308 is no greater than fifteen-gauge. In at least some embodiments, the lateral circumference of the outer insertion needle 308 is no greater than fourteen-gauge. In at least some embodiments, the lateral circumference of the outer insertion needle 308 is no greater than thirteen-gauge. In at least some embodiments, the lateral circumference of the outer insertion needle 308 is no greater than twelve-gauge.

Figure 5:
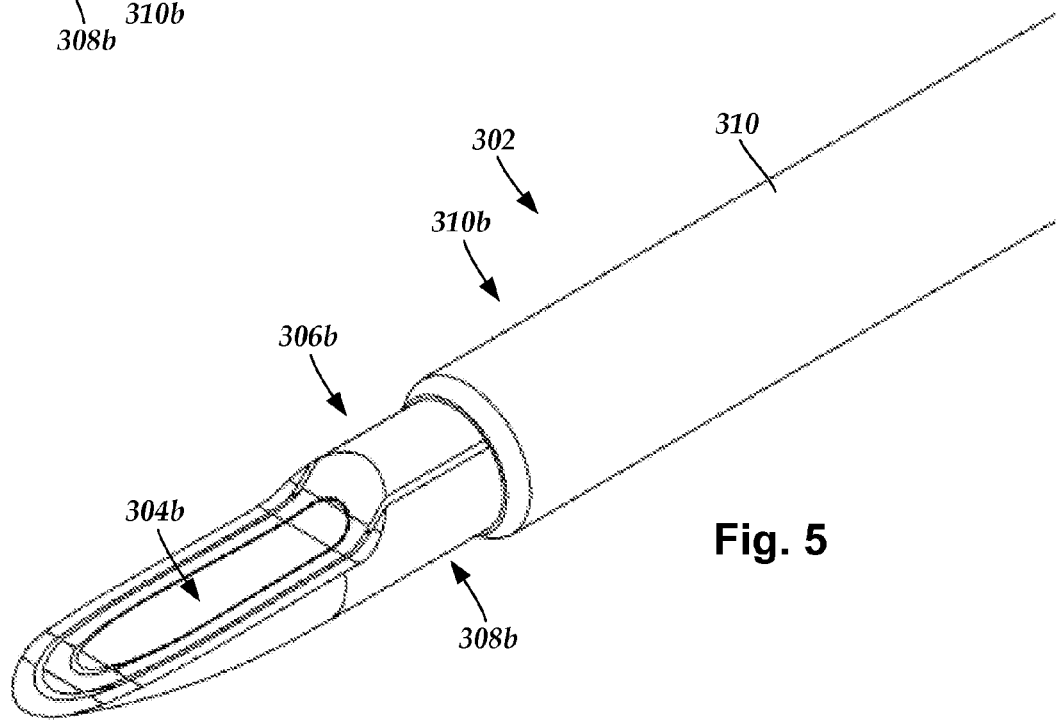
FIG. 5 is a schematic perspective close-up view of one embodiment of a distal end of the lead introducer of FIG. 3, according to the invention.

FIG. 5 is a schematic perspective close-up view of one embodiment of a distal end of the lead introducer 302. In at least some embodiments, the obturator 304, the inner insertion needle 306, the outer insertion needle 308, and the splitable member 310 coupleable to one another such that the distal ends 304b, 306b, and 308b of the obturator 304, the inner insertion needle 306, and the outer insertion needle 308, respectively, extend distally beyond the distal end 310b of the splitable member 310. In FIG. 5, the distal tips of the distal ends 304b and 306b of the obturator 304 and the inner insertion needle 306 are removed, for clarity of illustration. In at least some embodiments, the distal end 304b of the obturator 304 includes a blunt tip to reduce or prevent coring of patient tissue during insertion of the lead introducer 302 into a patient.

Figure 6:
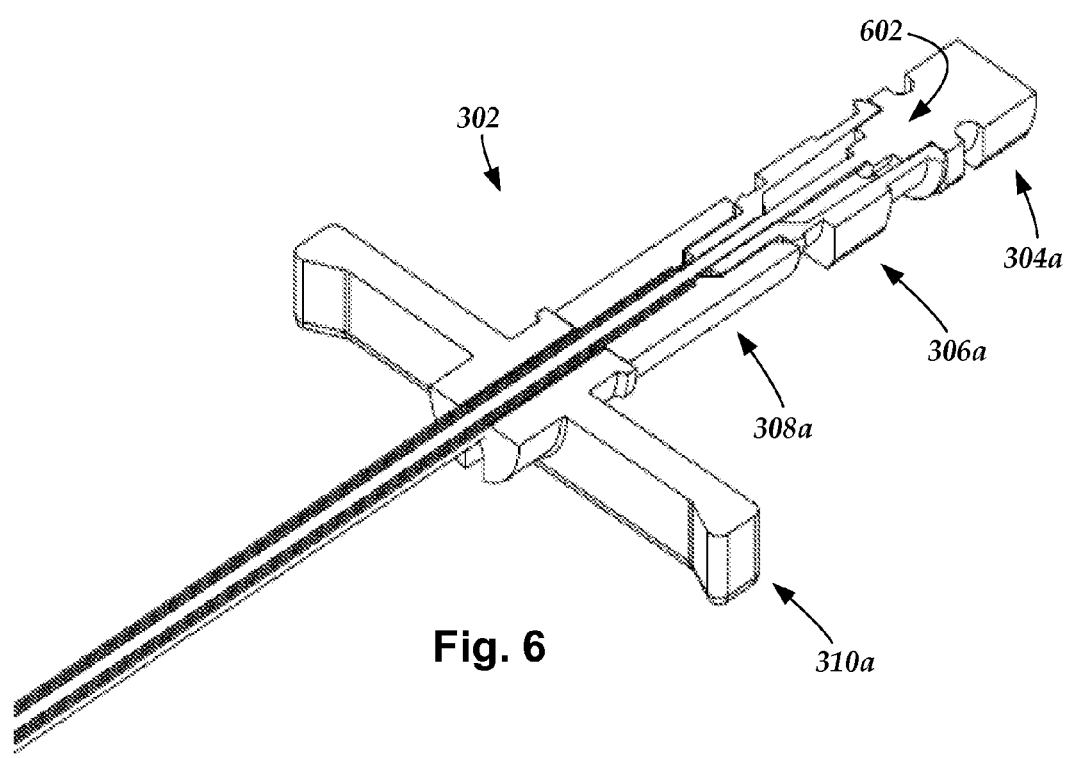
FIG. 6 is a schematic perspective longitudinal cross-sectional view of one embodiment of a proximal end of the lead introducer of FIG. 3, according to the invention.

FIG. 6 is a schematic perspective longitudinal cross-sectional view of one embodiment of a proximal end of the lead introducer 302. In FIG. 6, the obturator 304, the inner insertion needle 306, the outer insertion needle 308, and the splitable member 310 are coupleable to one another such that the proximal hubs 304a, 306a, 308a, and 310a of the obturator 304, the inner insertion needle 306, the outer insertion needle 308, and the splitable member 310, respectively, are axially aligned to one another.

In at least some embodiments, the proximal hub 306a of the inner insertion needle includes a luer fitting 602 configured and arranged to receive a syringe. In at least some embodiments, fluid (e.g., saline solution, air, or the like) may be introduced or removed through the luer fitting 602 to check for precise positioning of the lead introducer 302, for example, whether or not the epidural space has been entered.

Figure 7A:
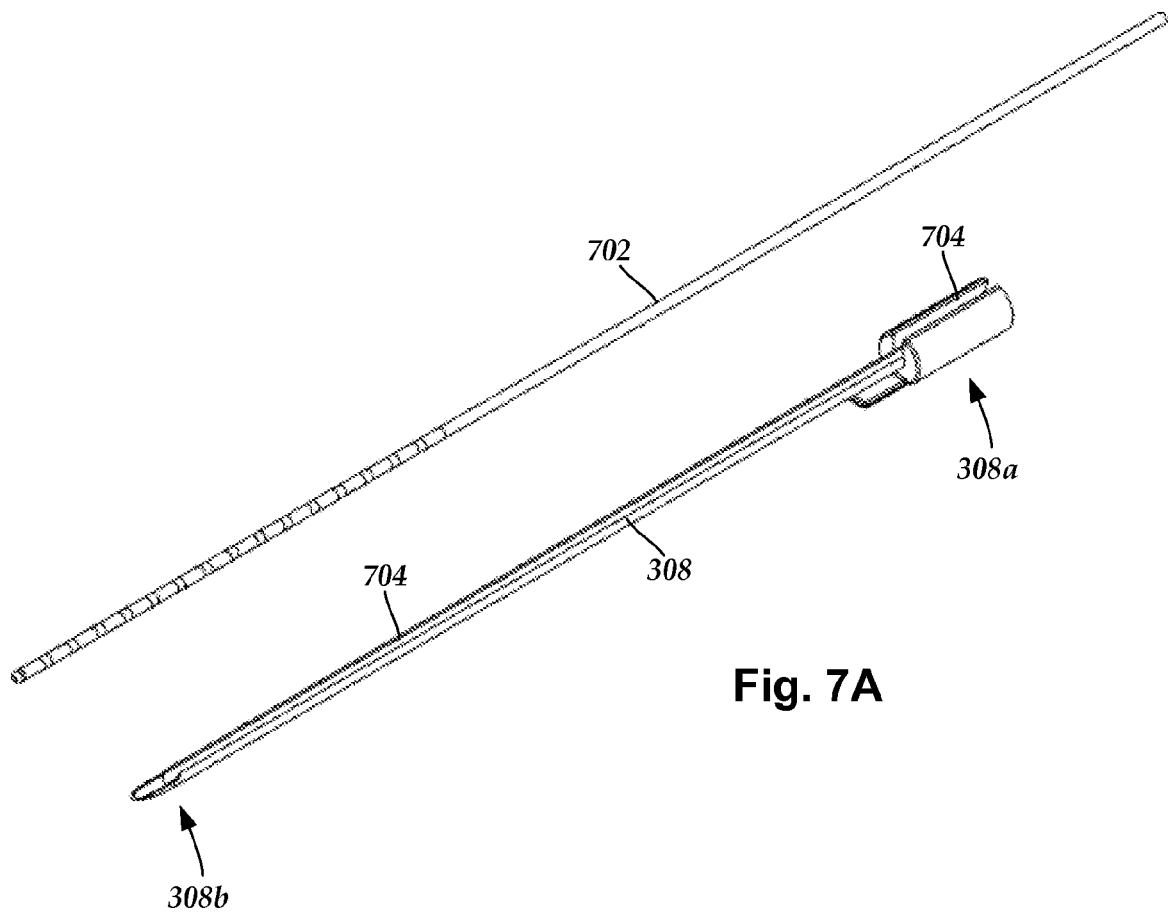
FIG. 7A is a schematic perspective view of one embodiment of a lead and an outer insertion needle of the lead introducer of FIG. 3, the outer insertion needle defining an open channel extending along a length of the outer insertion needle, the open channel configured and arranged to receive the lead, according to the invention.

In at least some embodiments, the outer insertion needle 308 is configured and arranged to receive a distal end of a lead when the inner insertion needle 306 is not disposed in the outer insertion needle 308. FIG. 7A is a schematic perspective view of one embodiment of a distal end of a lead 702 and the outer insertion needle 308 of the lead introducer 302. The outer insertion needle 308 defines an open channel 704 that extends substantially entirely along a length of the outer insertion needle 308 and that is configured and arranged to receive the distal end of the lead 702. In at least some embodiments, the open channel 704 extends along the proximal hub 310a of the outer insertion needle 308. In at least some embodiments, the open channel 704 extends along the entire length of the of the outer insertion needle 308.

In some embodiments, the lead 702 has an isodiametric lead body. In other embodiments, the lead 702 has a non-isodiametric lead body. In at least some embodiments, the lead 702 includes one or more elements (e.g., a junction, adaptor, or the like) disposed along the length of the lead 702 which have a transverse cross-sectional shape or size that is different from at least one other portion of the lead 702. In at least some embodiments, the distal end of the lead 702 has a transverse cross-sectional shape that is similar to the inner insertion needle 306. In at least some embodiments, the one or more elements having a different transverse cross-sectional shape or size are disposed on a proximal end of the lead 702.

In at least some embodiments, the inner insertion needle 306 is retained in the open channel 704 by the splitable member 310. In at least some embodiments, the inner insertion needle 306 is configured and arranged to at least substantially fill the open channel 704 when the inner insertion needle 306 is disposed in the open channel 704. In at least some embodiments, the inner insertion needle 306 is configured and arranged for insertion into and out of the open channel 704 of the outer insertion needle 308 by sliding the inner insertion needle 306 axially along the open channel 704.

In at least some embodiments, the open channel 704 is configured and arranged to receive the lead 702 when the inner insertion needle 306 is not disposed in the open channel 704. In at least some embodiments, the open channel 704 has a width that is no less than a diameter of the lead 702. In at least some embodiments, the open channel 704 is configured and arranged to receive the lead 702 such that the lead 702 may be separated from the open channel 704 without moving the lead 702 axially relative to the outer insertion needle 308.

In at least some embodiments, the lead 702 may be removed from the open channel 704 by applying enough lateral force to at least one of the lead 702 or the outer insertion needle 308 to pass the lead 702 out through the open channel 704. In at least some embodiments, the open channel 704 is configured and arranged such that, when the splitable member 310 is removed from the outer insertion needle 308, the lead 702 separates from the outer insertion needle 308 without needing to apply lateral force to either the lead 702 or the outer insertion needle 308.

Figure 7B:
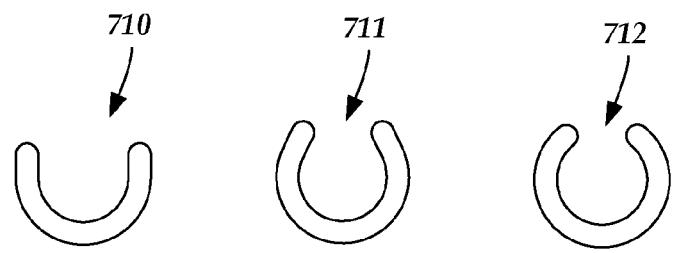
FIG. 7B is a schematic transverse cross-sectional view of several exemplary embodiments of the open channel of the outer insertion needle of FIG. 7A, according to the invention.

FIG. 7B is a schematic transverse cross-sectional view of several different exemplary embodiments of the open channel 704. In at least some embodiments, the portions of the outer insertion needle 308 along which the open channel 704 extends have a transverse cross-sectional shape that is at least substantially U-shaped 710. In at least some embodiments, the portions of the outer insertion needle 308 along which the open channel 704 extends have a transverse cross-sectional shape that is at least substantially horseshoe-shaped 711. In at least some embodiments, the portions of the outer insertion needle 308 along which the open channel 704 extends have a transverse cross-sectional shape that is at least substantially C-shaped 712.

In at least some embodiments, the lead 702 may be inserted into a patient using the lead introducer 302. In at least some embodiments, the obturator 304 is inserted into the lumen of the inner insertion needle 306, the inner insertion needle 306 is inserted into the open channel 704 of the outer insertion needle 308, and the outer insertion needle 308 is inserted into the splitable member 310, as shown in FIG. 3 and FIG. 4. It will be understood that the components of the lead introducer 302 can be assembled in any order. For example, the inner insertion needle 306 can be inserted into the open channel 704 of the outer insertion needle 308 either before or after the outer insertion needle 308 is inserted into the splitable member 310. In preferred embodiments, the lead introducer 302 is pre-assembled prior to insertion into the patient. In preferred embodiments, the lead introducer 302 is pre-assembled prior to a procedure to insert the lead introducer 302 into the patient.

The assembled lead introducer 302 is inserted into a patient and guided in proximity to a target stimulation location (e.g., several vertebrae levels above or below the target stimulation location). In at least some embodiments, once the lead introducer 302 is in proximity to a target stimulation location, the obturator 304 is removed and fluid is introduced or removed through the luer fitting 602 of the inner insertion needle 306 to check for precise positioning of the lead introducer 302, for example, in an epidural space of the patient.

Figure 8:
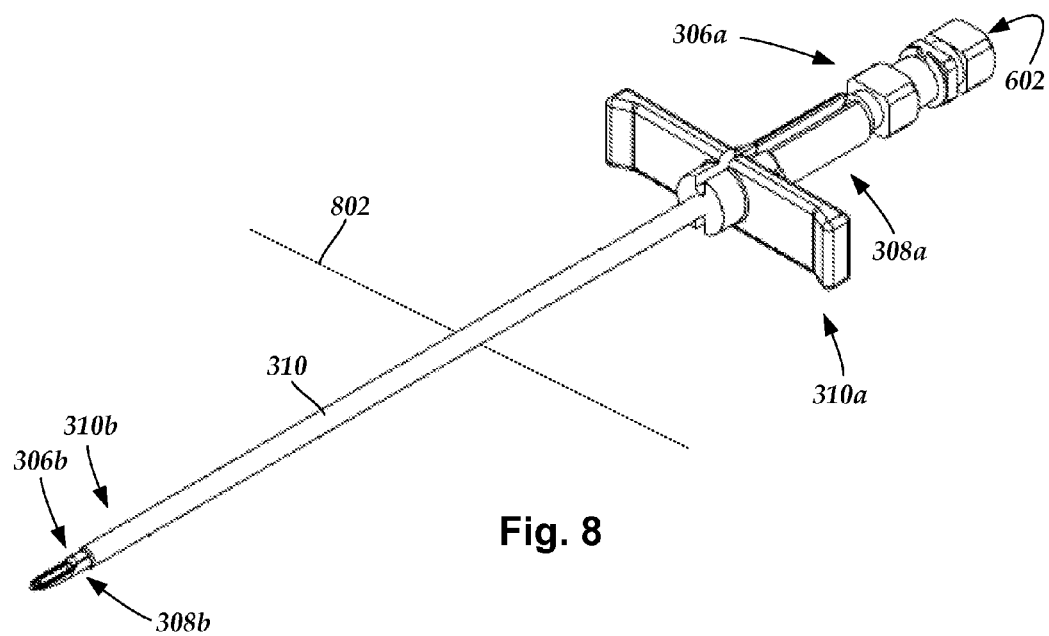
FIG. 8 is a schematic perspective view of one embodiment of an obturator removed from the lead introducer of FIG. 3, according to the invention.

FIG. 8 is a schematic perspective view of one embodiment of the inner insertion needle 306 inserted into the open channel 704 of the outer insertion needle 308 which, in turn, is inserted into the splitable member 310. In FIG. 8, the inner insertion needle 306, the outer insertion needle 308, and the splitable member 310 are disposed in a patient, as shown by a dotted line 802. The obturator 304 has been removed to allow access to the luer fitting 602 for performing the loss of resistance test. It will be understood that the assembled lead introducer 302 can also be inserted into a patient and guided in proximity to a target stimulation location without using the obturator 304.

Figure 9:
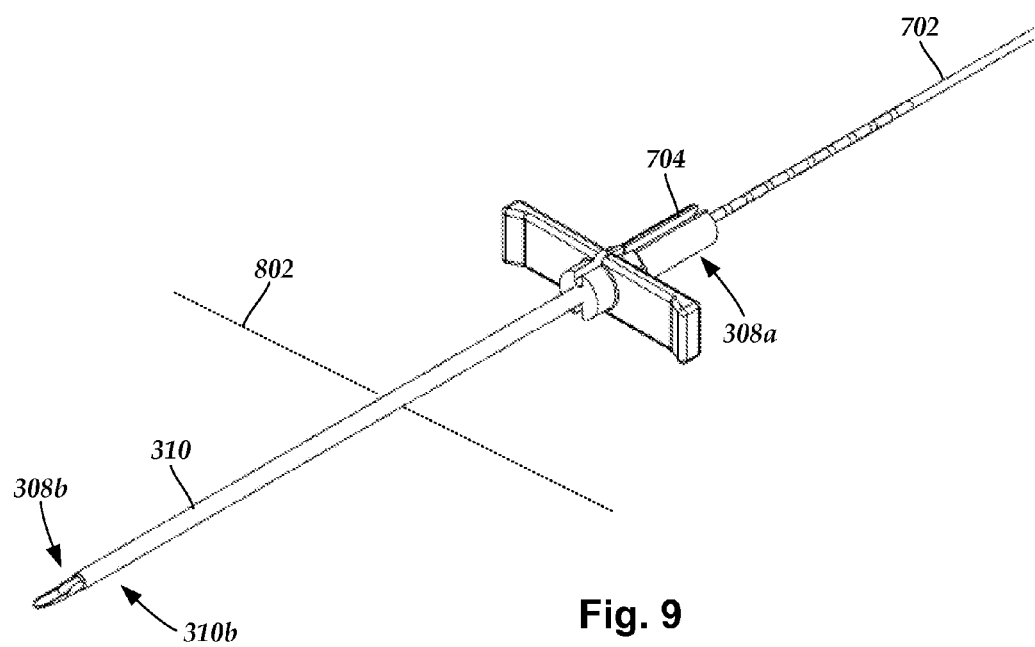
FIG. 9 is a schematic perspective view of one embodiment of an inner insertion needle removed from the lead introducer of FIG. 3 and replaced with the lead of FIG. 7A, according to the invention.

Once the lead introducer 302 is positioned in the epidural space in proximity to the target stimulation location, the inner insertion needle 306 may be removed and the distal end of the lead 702 may be inserted into the open channel 704 of the outer insertion needle 308. FIG. 9 is a schematic perspective view of one embodiment of the distal end of the lead 702 inserted into the open channel 704 of the outer insertion needle 308 via the proximal hub 308a. Once the distal end of the lead 702 is inserted into the open channel 704 of the outer insertion needle 308, the distal end of the lead 702 is guided to the target stimulation region. In at least some embodiments, the distal end of the lead 702 is guided to the target stimulation region by the comparably rigid outer insertion needle 308.

It may be an advantage to guide the lead 702 within the patient while the lead 702 is disposed in the outer insertion needle 308 and the splitable member 310. The outer insertion needle 308 and the splitable member 310 may provide the clinician with the ability to steer the lead introducer 302 by applying a laterally force of the lead introducer 302 to direct the trajectory of the lead 702. When the outer insertion needle 308 is removed from the lead 702 prior to insertion, then the splitable member 310 may be too flexible to provide this steering ability.

Once the distal end of the lead 702 has been guided to the target stimulation location, the splitable member 310 and the outer insertion needle 308 may be separated from the lead 702 and removed from the patient. It will be understood that the splitable member 310 may be separated from the lead 702 either before or after the outer insertion needle 308 is separated from the lead 702. It will also be understood that the splitable member 310 may be removed from the patient either before or after the outer insertion needle 308 is removed from the patient. In some embodiments, the outer insertion needle 308 is separated from the lead 702 prior to the splitable member 310 being separated from the lead 702. In other embodiments, the splitable member 310 is separated from the lead 702 prior to the outer insertion needle 308 being separated from the lead 702. In some embodiments, the outer insertion needle 308 is removed from the patient prior to removal of the splitable member 310. In other embodiments, the splitable member 310 is removed from the patient prior to removal of the outer insertion needle 308.

In preferred embodiments, the lead 702 is guided to the target stimulation location while disposed in the outer insertion needle 308 and the splitable member 310. The outer insertion needle 308 is removed from the lead 702 (and from the patient). The splitable member 310 is then split apart from the lead 702 and removed from the patient.

Figure 10:
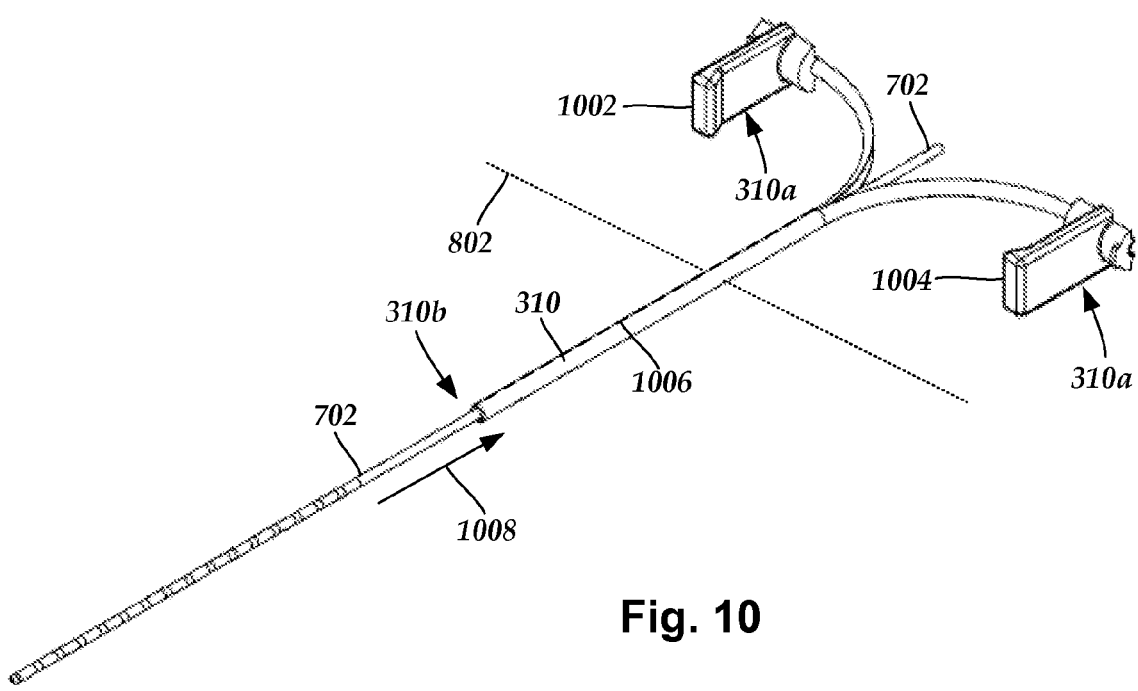
FIG. 10 is a schematic perspective view of one embodiment of a splitable member of the lead introducer of FIG. 3 being split apart to remove the splitable member from the lead of FIG. 7A, according to the invention.

FIG. 10 is a schematic perspective view of one embodiment of the splitable member 310 being split apart to remove the splitable member 310 from the lead 702. The proximal hub 310a of the splitable member 310 includes at least two pull-apart tabs 1002 and 1004.

In at least some embodiments, the splitable member 310 is formed from a flexible material suitable for implantation into the patient 802 including, for example, fluorinated ethylene propylene, polytetrafluoroethylene, high-density polyethylene, polyetheretherketone, and the like or combinations thereof. Additionally, one or more radiopaque materials may be added including, for example, barium sulfate and bismuth subcarbonate, and the like or combinations thereof to facilitate implantation of the introducer sheath through the use of one or more medical imaging techniques, such as fluoroscopy.

In at least some embodiments, the splitable member includes one or more weakened regions 1006, such as score lines or perforations, extending along at least a portion of a length of the splitable member 310 from between the at least two pull-apart tabs 1002 and 1004. In at least some embodiments, when the at least two pull-apart tabs 1002 and 1004 are separated from one another, for example, by pulling each pull-apart tab away from the other pull-apart tab(s) in directions approximately orthogonal to the splitable member 310, the splitable member 310 separates along the one or more weakened regions 1006.

In at least some embodiments, the splitable member 310 is separated into a plurality of longitudinal strips while pulling the splitable member 310 proximally along the lead 702. As the splitable member 310 splits apart, the distal end 310b of the splitable member 310 moves proximally along the lead 702 (as shown by arrow 1008), with an increasing amount of the lead 702 extending through the distal end 310b of the splitable member 310. In at least some embodiments, an undersurface of the splitable member 310 includes a lubricious coating to facilitate the proximal movement of the splitable member 310.

Eventually, the splitable member 310 may be completely separated into two or more longitudinal strips, thereby separating completely from the lead 702 and also from the patient. In at least some embodiments, the distal ends of the splitable member 310 may be extracted from the patient as the splitable member 310 is split apart. In at least some embodiments, the splitable member 310 may be split apart without causing the lead 702 to move.

Once the lead 702 is positioned at the target stimulation site, the lead 702 may be coupled to a control module (e.g., 102 of FIG. 1) and implanted using well-known techniques, for example, using one or more using tunneling straws placed in passageways underneath patient skin with bores that are sized large enough to receive the lead 702. In at least some embodiments, the lead 702 may be coupled to a connector of a control module, as shown in FIG. 3. In other embodiments, the lead 702 may be coupled to one or more other devices, including an adaptor, a lead extension, an operating room cable, or the like or combinations thereof.

Figure 11A:
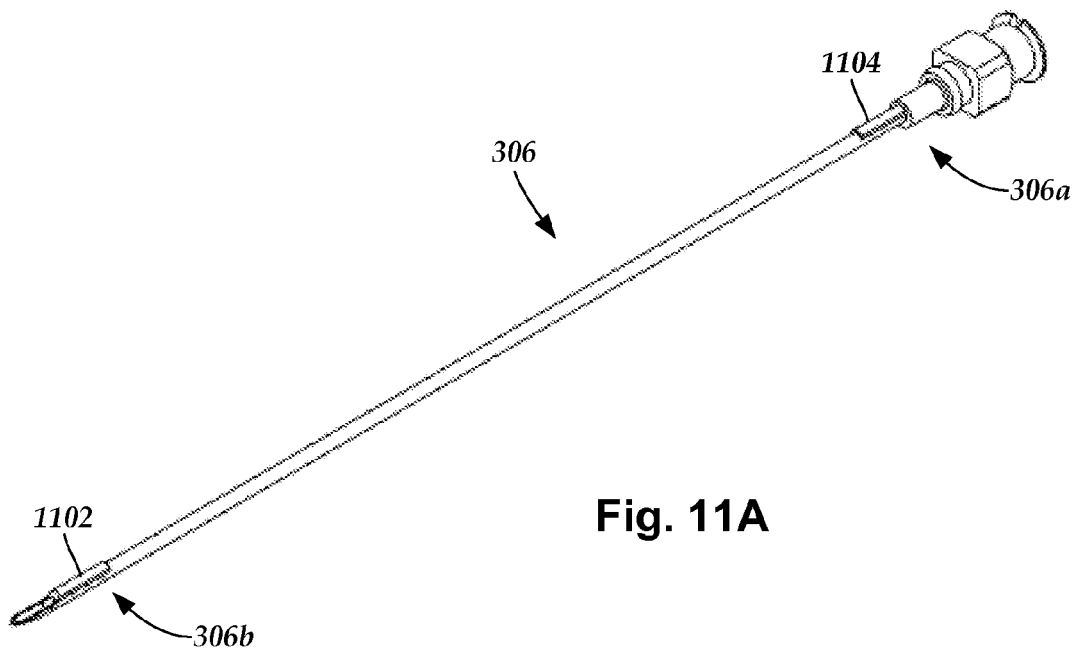
FIG. 11A is a schematic perspective view of one embodiment of a protrusion disposed at a distal end of an inner insertion needle, according to the invention.
Figure 11B:
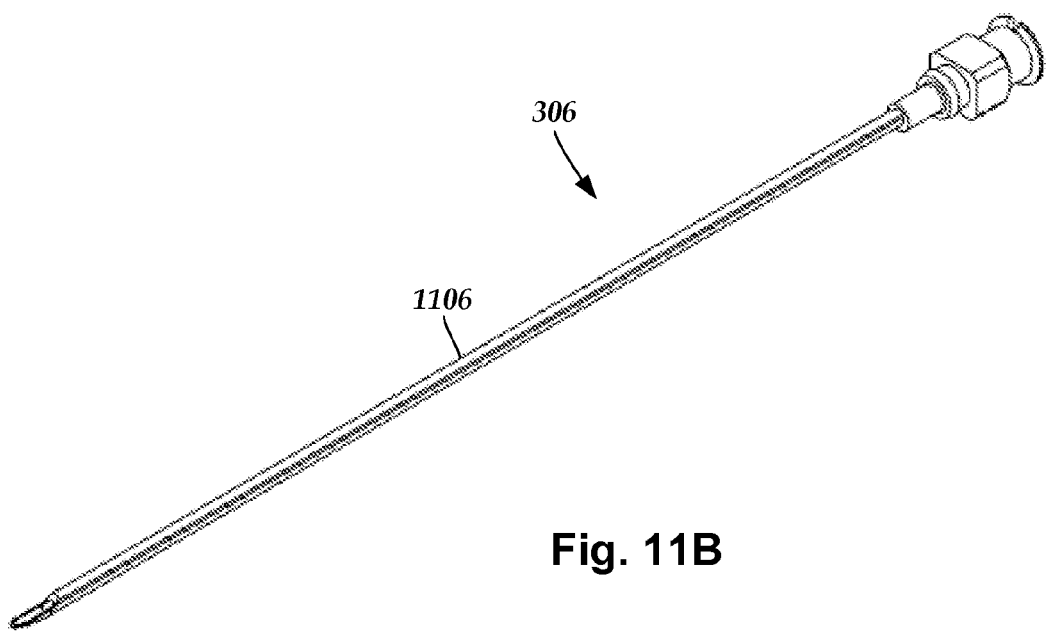
FIG. 11B is a schematic perspective view of one embodiment of a protrusion extending along at least a portion of a length of the inner insertion needle of FIG. 11A, according to the invention.

In at least some embodiments, the inner insertion needle 306 includes one or more protrusions that align with the open channel 704 to facilitate alignment of the inner insertion needle 306 in the open channel 704 of the outer insertion needle 308. FIG. 11A is a schematic perspective view of one embodiment of protrusions 1102 and 1104 disposed on the inner insertion needle 306. The protrusion 1102 is disposed at the distal end 306b of the inner insertion needle 306. The protrusion 1104 is disposed at the proximal hub 306a of the inner insertion needle 306. In preferred embodiments, the protrusions 1102 and 1104 are aligned with one another along the longitudinal axis of the inner insertion needle 306. In at least some embodiments, the inner insertion needle 306 includes only one of the protrusions 1102 or 1104. In at least some embodiments, the inner insertion needle 306 includes both the protrusions 1102 and 1104. In at least some embodiments, the insertion needle 306 includes one or more additional longitudinally-aligned protrusions. FIG. 11B is a schematic perspective view of one embodiment of a protrusion 1106 extending along at least a portion of a length of the inner insertion needle 306 between the proximal hub 306a and the distal end 306b.

Figure 12A:
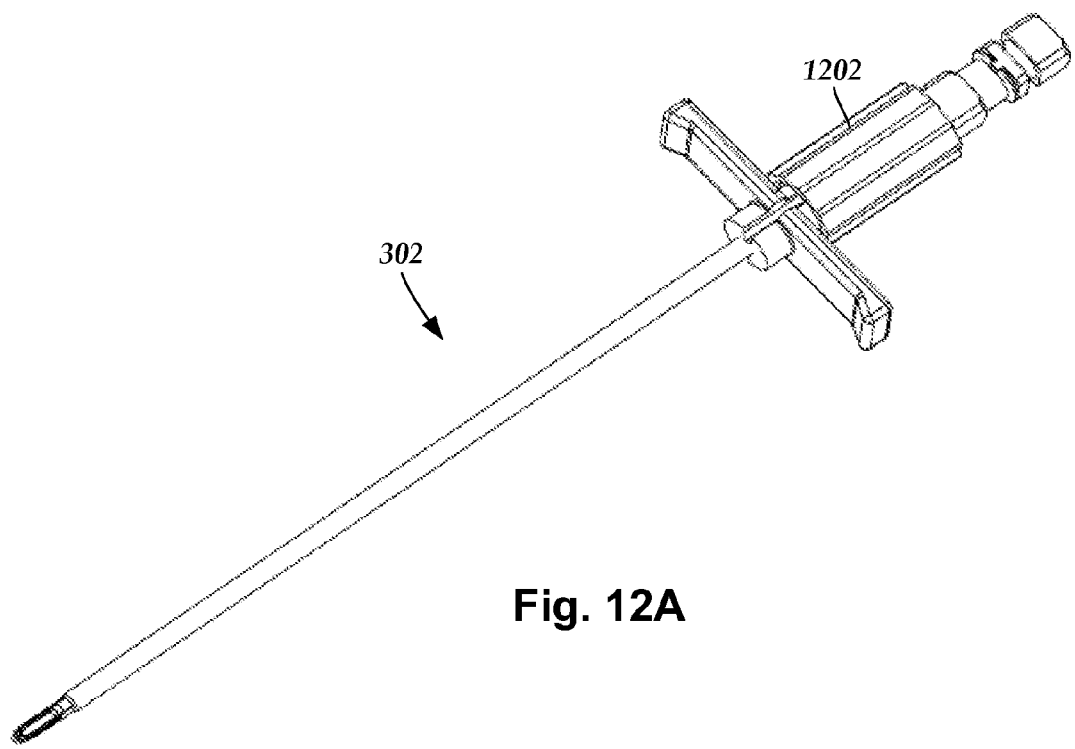
FIG. 12A is a schematic perspective view of one embodiment of a luer lock collar disposed over a proximal hub of the inner insertion needle of FIG. 11A, the luer lock collar locking the components of the lead introducer of FIG. 3 in place relative to one another, according to the invention.

In at least some embodiments, a luer lock collar may be disposed on the proximal hub 306a of the inner insertion needle 306 to lock the inner insertion needle 306, the outer insertion needle 308, and the splitable member 310 all together during insertion. FIG. 12A is a schematic perspective view of one embodiment of a luer lock collar 1202 disposed over the proximal hub 306a of the inner insertion needle 306. The luer lock collar 1202 is configured and arranged to lock the inner insertion needle 306, the outer insertion needle 308, and the splitable member 310 all together during insertion of the lead introducer 302 into the patient.

Figure 12B:
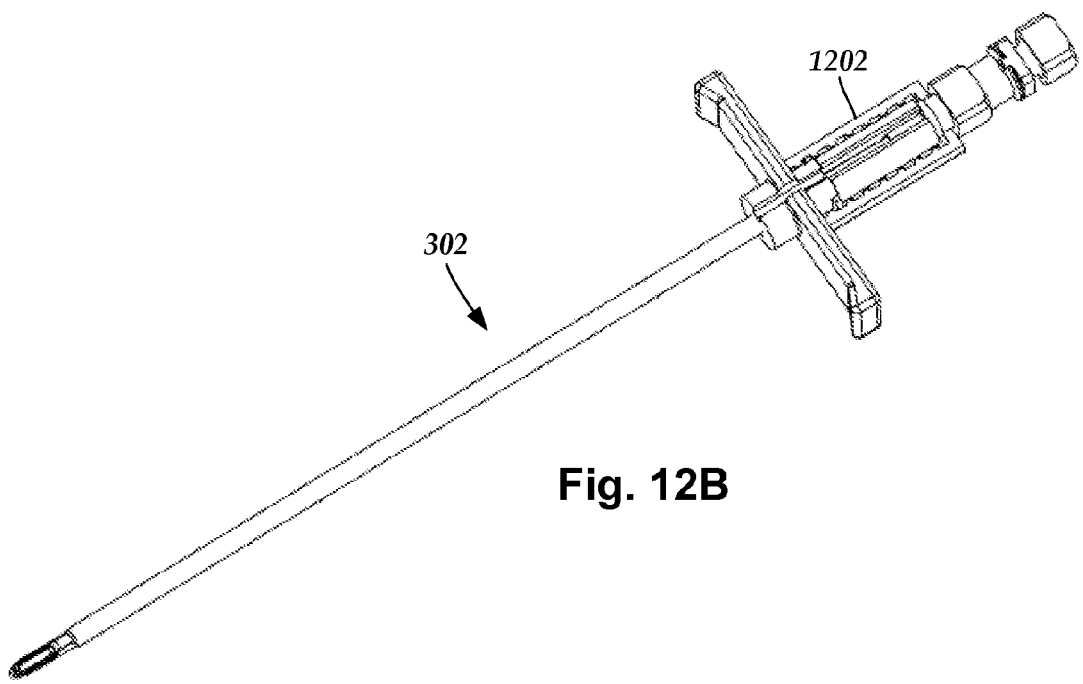
FIG. 12B is a schematic perspective view of one embodiment of the luer lock collar disposed over a proximal hub of the inner insertion needle of FIG. 11A, the luer lock collar shown being partially cut away for clarity of illustration, according to the invention.
Figure 12C:
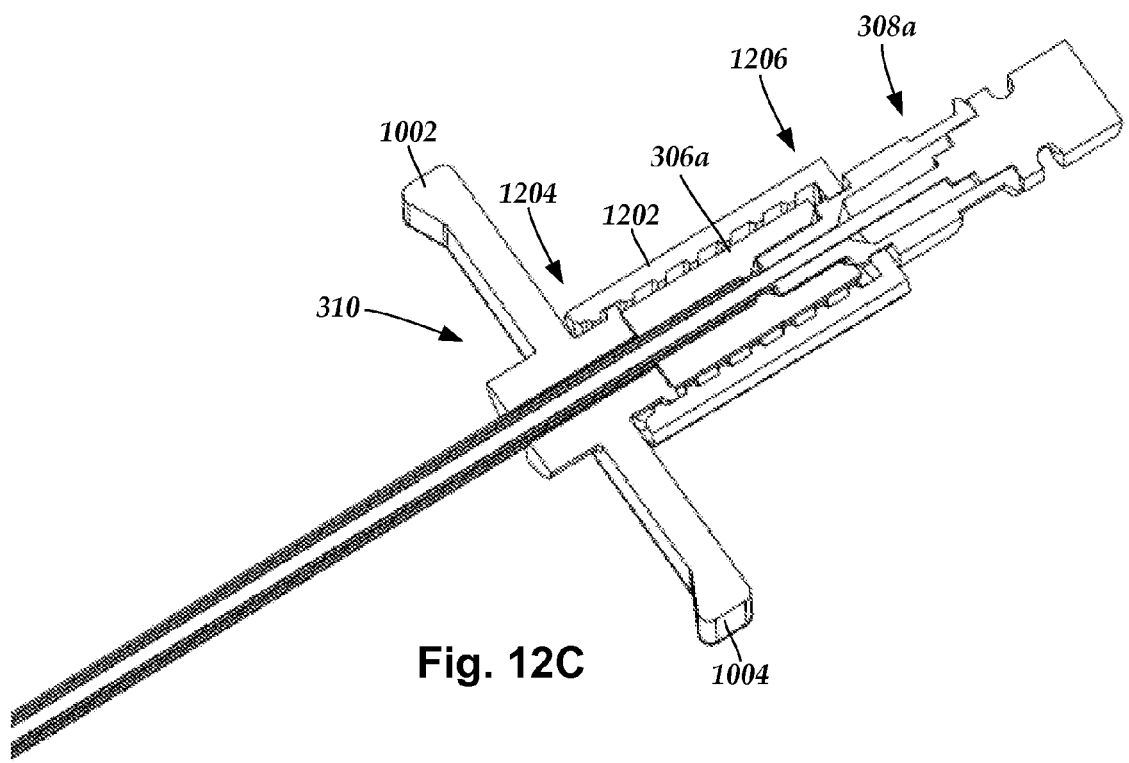
FIG. 12C is a schematic perspective, longitudinal cross-sectional view of one embodiment of a proximal end of the lead introducer of FIG. 3, where the luer lock collar of FIG. 12A is disposed over a proximal hub of the inner insertion needle of FIG. 11A, according to the invention.

FIG. 12B is a schematic perspective view of one embodiment of a luer lock collar 1202 disposed over the proximal hub 306a of the inner insertion needle 306. In FIG. 12B, the luer lock collar 1202 is shown partially cut away for clarity of illustration. FIG. 12C is a schematic perspective, longitudinal cross-sectional view of one embodiment of a proximal end of the lead introducer 302. The luer lock collar 1202 is disposed over the proximal hub 306a of the inner insertion needle 306. In at least some embodiments, a distal end 1204 of the luer lock collar 1202 is configured and arranged to mate with the pull-apart tabs 1002 and 1004 of the splitable member 310. In at least some embodiments, a proximal end 1206 of the luer lock collar 1202 is configured and arranged to mate with the proximal hub 308a of the outer insertion needle 308.

Figure 13:
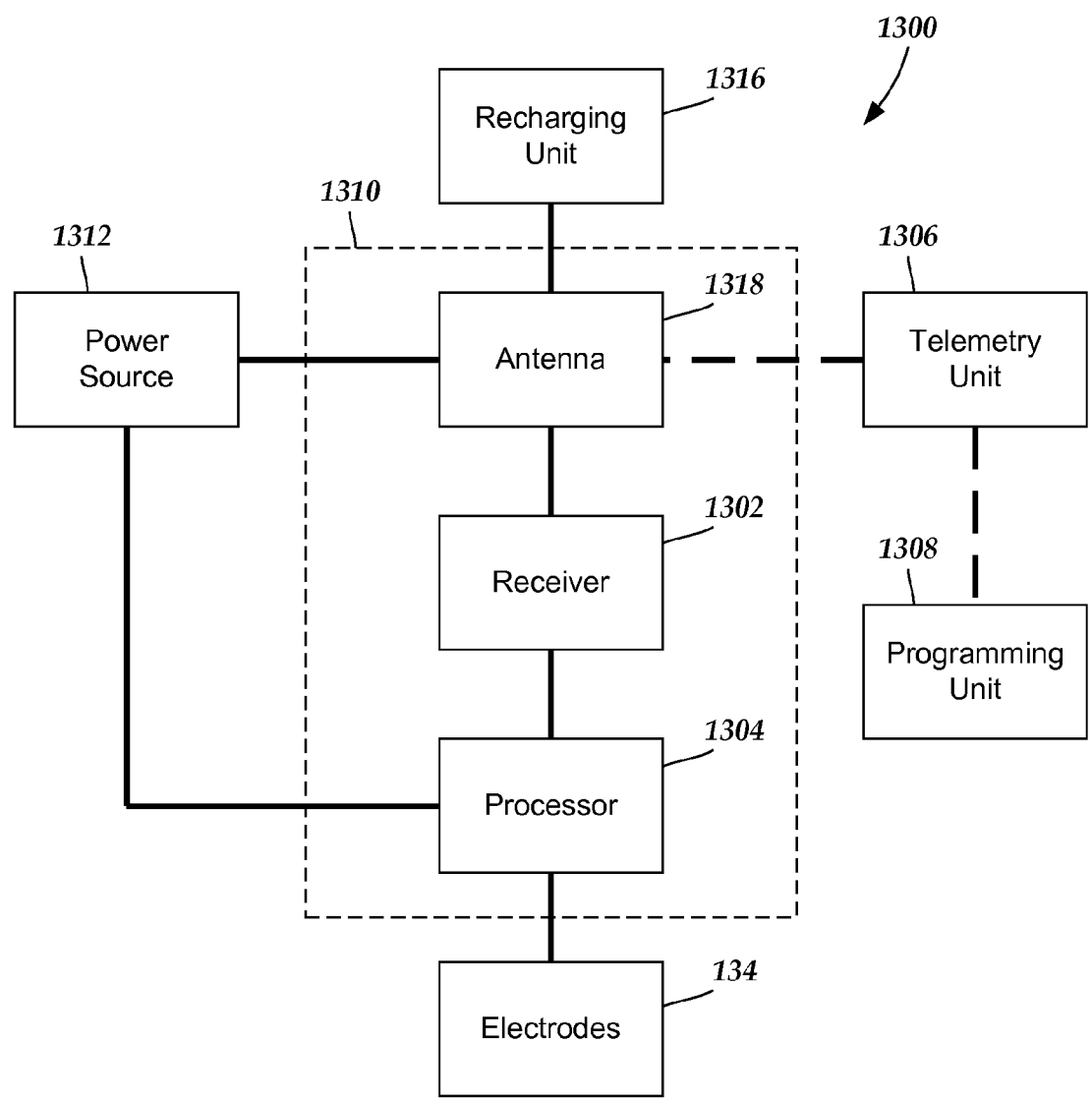
FIG. 13 is a schematic overview of one embodiment of components of a stimulation system, including an electronic subassembly disposed within a control module, according to the invention.

FIG. 13 is a schematic overview of one embodiment of components of an electrical stimulation system 1300 including an electronic subassembly 1310 disposed within a control module. It will be understood that the electrical stimulation system can include more, fewer, or different components and can have a variety of different configurations including those configurations disclosed in the stimulator references cited herein.

Some of the components (for example, power source 1312, antenna 1318, receiver 1302, and processor 1304) of the electrical stimulation system can be positioned on one or more circuit boards or similar carriers within a sealed housing of an implantable pulse generator, if desired. Any power source 1312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1318 or a secondary antenna. The external power source can be in a device that is mounted on the skin of the user or in a unit that is provided near the user on a permanent or periodic basis.

If the power source 1312 is a rechargeable battery, the battery may be recharged using the optional antenna 1318, if desired. Power can be provided to the battery for recharging by inductively coupling the battery through the antenna to a recharging unit 1316 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1304 is generally included to control the timing and electrical characteristics of the electrical stimulation system. For example, the processor 1304 can, if desired, control one or more of the timing, frequency, strength, duration, and waveform of the pulses. In addition, the processor 1304 can select which electrodes can be used to provide stimulation, if desired. In some embodiments, the processor 1304 may select which electrode(s) are cathodes and which electrode(s) are anodes. In some embodiments, the processor 1304 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1308 that, for example, allows modification of pulse characteristics. In the illustrated embodiment, the processor 1304 is coupled to a receiver 1302 which, in turn, is coupled to the optional antenna 1318. This allows the processor 1304 to receive instructions from an external source to, for example, direct the pulse characteristics and the selection of electrodes, if desired.

In one embodiment, the antenna 1318 is capable of receiving signals (e.g., RF signals) from an external telemetry unit 1306 which is programmed by a programming unit 1308. The programming unit 1308 can be external to, or part of, the telemetry unit 1306. The telemetry unit 1306 can be a device that is worn on the skin of the user or can be carried by the user and can have a form similar to a pager, cellular phone, or remote control, if desired. As another alternative, the telemetry unit 1306 may not be worn or carried by the user but may only be available at a home station or at a clinician's office. The programming unit 1308 can be any unit that can provide information to the telemetry unit 1306 for transmission to the electrical stimulation system 1300. The programming unit 1308 can be part of the telemetry unit 1306 or can provide signals or information to the telemetry unit 1306 via a wireless or wired connection. One example of a suitable programming unit is a computer operated by the user or clinician to send signals to the telemetry unit 1306.

The signals sent to the processor 1304 via the antenna 1318 and receiver 1302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1300 to cease operation, to start operation, to start charging the battery, or to stop charging the battery. In other embodiments, the stimulation system does not include an antenna 1318 or receiver 1302 and the processor 1304 operates as programmed.

Optionally, the electrical stimulation system 1300 may include a transmitter (not shown) coupled to the processor 1304 and the antenna 1318 for transmitting signals back to the telemetry unit 1306 or another unit capable of receiving the signals. For example, the electrical stimulation system 1300 may transmit signals indicating whether the electrical stimulation system 1300 is operating properly or not or indicating when the battery needs to be charged or the level of charge remaining in the battery. The processor 1304 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead introducer comprising:
    a multi-piece insertion needle comprising
        an outer insertion needle comprising a proximal hub and defining an open channel that extends along an entire length of the outer insertion needle and the proximal hub, and
        an inner insertion needle comprising a proximal hub and defining a lumen that extends from the proximal hub along the inner insertion needle, the inner insertion needle configured and arranged for insertion into the open channel of the outer insertion needle; and
    a splitable member comprising a proximal hub and defining a lumen configured and arranged for receiving at least a portion of the multi-piece insertion needle, the splitable member comprising
        at least two pull-apart tabs disposed on the proximal hub of the splitable member, and
        at least one weakened region extending along at least a portion of a length of the splitable member from between the at least two pull-apart tabs, the at least one weakened region configured and arranged for separating when the at least two pull-apart tabs are pulled apart from one another in directions approximately orthogonal to the splitable member.

2. The implantation system of claim 1, further comprising an obturator configured and arranged for insertion into the lumen of the inner insertion needle.

3. The implantation system of claim 2, wherein the obturator comprises a blunt distal tip and a proximal hub that aligns axially with the proximal hub of the inner insertion needle when the obturator is inserted into the lumen of the inner insertion needle.

4. The implantation system of claim 1, wherein the inner insertion needle comprises at least one protrusion configured and arranged for insertion into the open channel of the outer insertion needle.

5. The implantation system of claim 1, wherein the proximal hub of the inner insertion needle comprises a luer fitting.

6. The implantation system of claim 5, further comprising a luer lock collar configured and arranged for disposing over at least a portion of the proximal hub of the inner insertion needle.

7. The implantation system of claim 1, wherein outer insertion needle is more rigid than the splitable member.

8. An insertion kit comprising:
    the implantation system of claim 1;
    a neurostimulation lead with a distal end configured and arranged for implantation into a patient, the neurostimulation lead comprising
        a lead body having a distal end and a proximal end,
        a plurality of electrodes disposed at the distal end of the lead body,
        a plurality of terminals disposed at the proximal end of the lead body, and
        a plurality of conductive wires coupling the plurality of electrodes electrically to the plurality of terminals; and
    wherein the open channel of the outer insertion needle is configured and arranged such that, when the inner insertion needle is not inserted in the open channel, the distal end of the lead body is insertable into the open channel such that the lead body is laterally separable from the outer insertion needle through the open channel.

9. The insertion kit of claim 8, wherein the distal end of the lead body is insertable into the open channel such that the lead body is laterally separable from the outer insertion needle through the open channel without moving the lead body axially along a length of the outer insertion needle during separation.

10. The insertion kit of claim 8, wherein the lead body is non-isodiametric.

11. The insertion kit of claim 8, wherein the neurostimulation lead further comprises one or more elements disposed along a length of the lead body that has a transverse cross-sectional shape or size that is different from the transverse cross-sectional shape or size of the lead body.

12. An electrical stimulation system comprising:
    the insertion kit of claim 8;
    a control module configured and arranged to electrically couple to the proximal end of the lead body, the control module comprising
        a housing, and
        an electronic subassembly disposed in the housing; and
    a connector for receiving the neurostimulation lead of the insertion kit, the connector comprising
        a connector housing defining a port for receiving the proximal end of the lead body of the neurostimulation lead, and
        a plurality of connector contacts disposed in the connector housing, the connector contacts configured and arranged to couple to the plurality of terminals disposed at the proximal end of the lead body.

13. The electrical stimulation system of claim 12, wherein the connector is disposed on the control module.

14. The electrical stimulation system of claim 12, further comprising a lead extension having a proximal end and a distal end, the connector disposed on the distal end of the lead extension.

15. The electrical stimulation system of claim 14, wherein the proximal end of the lead extension is configured and arranged for insertion into another connector.

16. A method for implanting a neurostimulation lead into a patient, the method comprising:
    providing the lead introducer of claim 1;
    guiding the splitable member with the inner insertion needle and the outer insertion needle to a position within the patient;
    removing the inner insertion needle from the patient, leaving the outer insertion needle and splitable member in the patient;
    inserting into the open channel of the outer insertion needle a distal end of a neurostimulation lead, the neurostimulation lead comprising a plurality of electrodes disposed along a distal end of the neurostimulation lead and a plurality of terminals disposed along at least one proximal end of the neurostimulation lead;

separating the outer insertion needle from the neurostimulation lead by passing the neurostimulation lead laterally through the open channel of the outer insertion needle;

removing the outer insertion needle from the patient, leaving the neurostimulation lead disposed in the splitable member;

separating the splitable member into at least two parts along the length of the lumen of the splitable member; and removing the splitable member from the patient, leaving the distal end of the neurostimulation lead implanted in the patient at a target stimulation location.

17. The method of claim 16, wherein the steps of separating the outer insertion needle from the neurostimulation lead and removing the outer insertion needle from the patient are performed subsequent to separating the splitable member into at least two parts along the length of the lumen of the splitable member and removing the splitable member from the patient.

18. The method of claim 17, wherein guiding the splitable member with the inner insertion needle and the outer insertion needle to a position within the patient comprises guiding the splitable member, the inner insertion needle, and the outer insertion needle to the position within the patient, wherein an obturator is disposed in the inner insertion needle, and removing the obturator from the inner insertion needle.

19. The method of claim 16, wherein guiding the splitable member with the outer insertion needle and the neurostimulation lead to a target stimulation location within the patient comprises using the outer insertion needle to guide the splitable member and the neurostimulation lead to the target stimulation location within the patient.

20. The implantation system of claim 1, wherein the lumen of the inner insertion needle extends an entire length of the inner insertion needle.

* * * * *